US00PP24728P3

(12) United States Plant Patent
Bédard

(10) Patent No.: US PP24,728 P3
(45) Date of Patent: Aug. 5, 2014

(54) FLORIBUNDA ROSE PLANT NAMED 'WEKCISFRABO'

(50) Latin Name: *Rosa hybrida*
Varietal Denomination: WEKcisfrabo

(71) Applicant: Early Morning LLC, Pomona, CA (US)

(72) Inventor: Christian Bédard, Brea, CA (US)

(73) Assignee: Early Morning LLC, Pomona, CA (US)

( * ) Notice: Subject to any disclaimer, the term of this patent is extended or adjusted under 35 U.S.C. 154(b) by 114 days.

(21) Appl. No.: 13/694,322

(22) Filed: Nov. 19, 2012

(65) Prior Publication Data

US 2014/0143918 P1 May 22, 2014

(51) Int. Cl.
*A01H 5/00* (2006.01)

(52) U.S. Cl.
USPC ..... Plt./151; Plt./141

(58) Field of Classification Search
USPC ..... Plt./151, 141
See application file for complete search history.

(56) References Cited

U.S. PATENT DOCUMENTS

PP12,001 P2 7/2001 Kordes
PP13,513 P2 1/2003 Carruth

*Primary Examiner* — Susan McCormick Ewoldt
(74) *Attorney, Agent, or Firm* — McKee, Voorhees & Sease, P.L.C.

(57) ABSTRACT

A new variety of Floribunda rose suitable for garden decoration, having flowers of deep velvet red coloration.

1 Drawing Sheet

Classification: The present invention relates to a new *Rosa hybrida* plant.

Variety denomination: The new plant has the varietal denomination 'WEKcisfrabo'.

BACKGROUND OF THE INVENTION

This invention relates to a new and distinct variety of Floribunda Rose. It has as its seed parent the variety known as 'WEKsanpoly' (U.S. Plant Pat. No. 13,513) and as its pollen parent the variety known as 'KORbeteilich' (U.S. Plant Pat. No. 12,001).

SUMMARY OF THE INVENTION

Among the features which distinguish the new variety from other presently available and commercial rose cultivars known to the inventor are the following combinations of characteristics: its deep velvet red coloration that does not burn under intense sunlight, its excellent color stability throughout the life of the flower and its red suffusion on the inner surface of the sepal that appears as the flower ages. The plant has an upright moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKcisfrabo' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'WEKsanpoly' by the following combination of characteristics: whereas 'WEKcisfrabo' bears medium to somewhat large sized flowers (about 8.0 to about 11.1 cm. in diameter) of deep velvet red coloration, 'WEKsanpoly' bears significantly smaller flowers (about 6.5 to about 9.0 cm. in diameter) of even medium red coloration. The new variety has an upright moderately spreading somewhat tall growing habit (about 120 to about 180 cm. in height), whereas the seed parent has a rounded bushy to somewhat upright significantly shorter growing habit (about 88 to about 105 cm. in height).

The new variety may be distinguished from its pollen parent, 'KORbeteilich' by the following combination of characteristics: whereas 'WEKcisfrabo' bears double flowers (about 18 to 28 petals) of deep velvet red coloration, 'KORbeteilich' bears double flowers of bright red coloration with heavier petalage (about 25 to 30 petals). The new variety has an upright moderately spreading somewhat tall growing habit (about 120 to about 180 cm. in height and about 150 to about 190 cm. spread at the widest point), whereas the pollen parent has a more upright and less spreading growing habit (about 155 to about 170 cm. in height and about 108 cm. spread at the widest point).

COMPARISON WITH THE CLOSEST COMMERCIALLY AVAILABLE CULTIVAR

The closest commercially available cultivar to the new variety is the pollen parent 'KORbeteilich' (U.S. Plant Pat. No. 12,001).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety sometimes bears its flowers singly, sometimes in clusters of two to three per stem. Flowers may be borne in regular rounded clusters on strong short to medium length stems (about 22 to about 66 cm.). Outdoors, the plant blooms abundantly and nearly continuously during the growing season. The flowers have a slight tea to somewhat spicy fragrance.

BUD

The peduncle is about 3.4 to about 6.3 cm. in length, of average to somewhat heavy caliper (about 0.2 to about 0.4 cm. in diameter), and usually erect. It is moderately rough, with some stipitate glands and very few hairs. Peduncle color is between 146B and 146C often heavily suffused, especially on the side exposed to the sun, with between 187B and 187A.

Before the calyx breaks, the bud is about 1.0 to about 1.6 cm. in diameter at the widest point, about 1.4 to about 2.2 cm. in length, and pointed to somewhat ovoid in shape. The surface of the bud bears between 9 to 13 foliaceous appendages, few hairs and few stipitate glands, usually with stout much cut foliaceous parts extending beyond the tip of the bud about ¾ or more of its length. Bud color is between 137B and 137C often heavily suffused, especially on the side exposed to the sun, with between 187A and 187B.

The sepals are about 3.1 to about 4.7 cm. in length and about 0.8 to about 1.2 cm. in width at the widest point. The outer surface color of the sepal is between 137B and 137C often heavily suffused, especially on the side exposed to the sun, with between 187A and 187B. The outer surface of the sepal is smooth and bears between 2 to 5 foliaceous appendages with few stipitate glands and hairs. The inner surface color of the sepal is near 146C broadly bordered by near 137A. After the sepals open, the inner surface color is often heavily suffused, especially on the area exposed to the sun, with between 187A and 187B. The inner surface of the sepal is covered with fine wooly tomentum; sepal margins are lined with very few stipitate glands and numerous hairs.

The receptacle of the flower is of medium length (about 0.4 to about 0.6 cm.) and somewhat heavy in caliper (about 0.5 to about 0.8 cm. in diameter). The receptacle is urn-shaped in form. Its surface is smooth with moderately thin fleshy walls. The receptacle color is between 144A and 143C sometimes lightly suffused, especially on the side exposed to the sun, with between 187B and 187C.

As the petals open (after the calyx breaks), the bud is about 1.6 to about 2.0 cm. in diameter at the widest point, about 2.1 to about 2.7 cm. in length, and ovoid to somewhat pointed in form. The color of the under and upper surfaces of the newly opened petals is between 187A and 187B. At the point where the petal attaches, there is a moderately small zone of between 154C and 1C.

BLOOM

When fully open, the bloom ranges from about 8.0 to about 11.1 cm. in diameter. Petalage is double with about 18 to 28 petals and about 4 to 7 petaloids irregularly arranged. When partially open, the bloom form is somewhat high centered to moderately cupped, and the petals are loosely spiraled to cupped with petal edges somewhat reflexed outward. When fully open, the bloom form is more cupped, and the petals are loosely cupped to slightly undulated with petal edges moderately reflexed outward.

PETALS

The substance of the petals is moderately heavy and of somewhat thick thickness, with upper surfaces velvety to moderately satiny and under surfaces shiny. The petals are about 2.8 to about 5.7 cm. in length and about 2.4 to about 5.5 cm. in width at the widest point. Petal margins are entire.

The outer petals are moderately obovate to somewhat rounded in shape with rounded apices.

The inner petals are obovate in shape with rounded apices.

Petaloids are about 1.0 to about 4.6 cm. in length and about 0.7 to about 4.1 cm. in width at the widest point. Petaloids are irregularly shaped somewhat obovate to oblanceolate with rounded apices.

NEWLY OPENED FLOWER

The under surface color of the outer, intermediate and inner petals is between 53C and 53B, sometimes moderately suffused, especially on the outermost petals, with near 53A. At the point where the petal attaches, there is a moderately small zone of between 1C and 154C. The upper surface color of the outer, intermediate and inner petals is between 46A and 53B sometimes moderately suffused, especially on the outermost petals, with near 53A. At the point where the petal attaches, there is a somewhat large zone of between 2C and 3D.

The under and upper surface colors of the petaloids are similar in coloration to the upper and under surfaces of the intermediate and inner petals.

The general tonality of the newly opened flower is between 46A and 53B sometimes moderately suffused with near 53A.

THREE-DAY-OLD FLOWER

The under and upper surface color of the outer, intermediate and inner petals is between 60B and 53B, sometimes moderately suffused, especially on the outermost petals, with between 53A and 60A. At the point where the petal attaches, there is a moderately small zone of between 2D and 4D. The upper surface color of the outer, intermediate and inner petals is between 46A and 53B often moderately suffused, especially on the outermost petals, with between 53A and 187B. At the point where the petal attaches, there is a somewhat large zone of near 4D.

The under and upper surface colors of the petaloids are similar in coloration to the upper and under surfaces of the intermediate and inner petals.

The general tonality of the three-day-old flower is between 46A and 53B often moderately suffused with between 53A and 187B.

On the spent bloom, the petals usually drop off cleanly, and are not particularly affected by cold, hot, wet, or dry weather.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 115) and are arranged regularly about the pistils; a few are mixed with petaloids. The filaments are of variable length (about 0.4 to about 1.6 cm.) most with anthers. Filaments are between 5C and 4A in color often moderately suffused with between 53B and 53C. The anthers are of medium size for the class and all open approximately at the same time. Anther color when immature is near 20A on the external part and near 18C on the internal part often moderately suffused with near 53B. Anther color at maturity is near 164D on the external part and near 200B on the internal part. Pollen is moderately abundant and between 18D and 19D in color.

FEMALE REPRODUCTIVE ORGANS

Pistils vary in number (average about 70). The styles are moderately even, somewhat long in length (about 0.7 to about 1.1 cm.), heavy in caliper, and loosely bunched to somewhat separated. Stigma color is between 11C and 12D. Style color is between 154D and 154C often heavily suffused with between 53A and 60A. Ovaries are usually all enclosed in the calyx.

Hips have not been observed on this variety when grown in Pomona, Calif.

FOLIAGE

The compound leaves are usually comprised of three to seven leaflets and are borne abundantly. The five-leaflet leaves are about 5.2 to about 12.2 cm. in length and about 6.6 to about 10.7 cm. in width at the widest point, leathery to somewhat crisp in texture, and moderately glossy in finish on the upper side and matte in finish on the under side. The leaves have a pinnate venation pattern. The terminal leaflets are about 2.7 to about 7.2 cm. in length and about 2.0 to about 4.3 cm. in width at the widest point, shaped ovate to somewhat oval with acute apices and rounded to somewhat acute bases. Their margins are usually simply serrate.

The upper surface color of the mature leaf is between 139A and 137B. The under surface color of the mature leaf is between 147B and 148B. The under and upper colors of the leaf veins on the mature leaf are similar in coloration to the upper and under surfaces colors of the mature leaf. The upper surface color of the young leaf is between 147A and 137B, often heavily suffused with between 187A and 187B. The under surface color of the young leaf is between 138A and 147B, often heavily suffused with between 187B and 187A. The under and upper colors of the leaf veins on the young leaf are similar in coloration to the upper and under surfaces colors of the young leaf.

The rachis is average in caliper and mostly smooth. The upper side is deeply grooved with few hairs and stipitate glands on the edges of the grooves. The under side of the rachis is mostly smooth with occasionally very few small prickles. The rachis color is near 146D on the under side and near 137C on the upper side often moderately suffused on the young leaves with between 187B and 187A.

The stipules are about 1.3 to about 1.6 cm. in length and moderately wide (about 0.5 to about 0.8 cm.) with medium to somewhat long straight points that usually turn out at an angle of more than 45 degrees and sometimes recurve toward the stem. The under and upper surface color of the stipule is between 137B and 137C sometimes moderately suffused on the young leaves with between 187A and 187B.

The petiole is average in caliper and mostly smooth. The upper side is deeply grooved with few hairs and stipitate glands on the edges of the grooves. The under side of the petiole is mostly smooth with occasionally very few small prickles. The petiole is about 0.4 to about 1.3 cm. in length and about 0.1 to about 0.2 cm in width at the widest point. The petiole color is near 146D on the under side and near 137C on the upper side often moderately suffused on the young leaves with between 187B and 187A.

The plant displays an above average degree of resistance to powdery mildew and rust as compared to other commercial varieties grown under comparable conditions in Pomona, Calif. The plant's winter hardiness and drought/heat tolerance are yet to be determined.

GROWTH

The plant has an upright moderately spreading somewhat tall growing habit (about 120 to about 180 cm. in height and about 150 to about 190 cm. spread at the widest point), with full branching. It displays moderately vigorous growth and the canes are of somewhat heavy caliper for the class (about 1.4 to about 2.3 cm. in diameter at the widest point).

The color of the major stems is between 146B and 146C. They bear some large prickles that are about 0.8 to about 1.1 cm. in length. The large prickles are almost straight, slightly angled downward with a moderately long somewhat broad oval base; prickle color is between 165A and 177A. The major stem bears few small prickles of similar shape and coloration.

The color of the branches is between 146B and 137B. They bear some large prickles which are of similar shape to the large prickles on the major stems. The prickles are about 0.5 to about 0.9 cm. in length. The prickle color is between 165B and 165C. The branches bear few small prickles of similar shape and coloration.

The color of the new shoots is between 146C and 146B often heavily suffused with between 187B and 187A. They bear some large prickles which are of similar size and shape to the large prickles on the branches; prickle color is between 146C and 146D often heavily suffused with between 187B and 187A. The shoots bear few small prickles of similar shape and coloration.

I claim:

1. A new and distinct Floribunda rose plant of the variety substantially as described and illustrated herein.

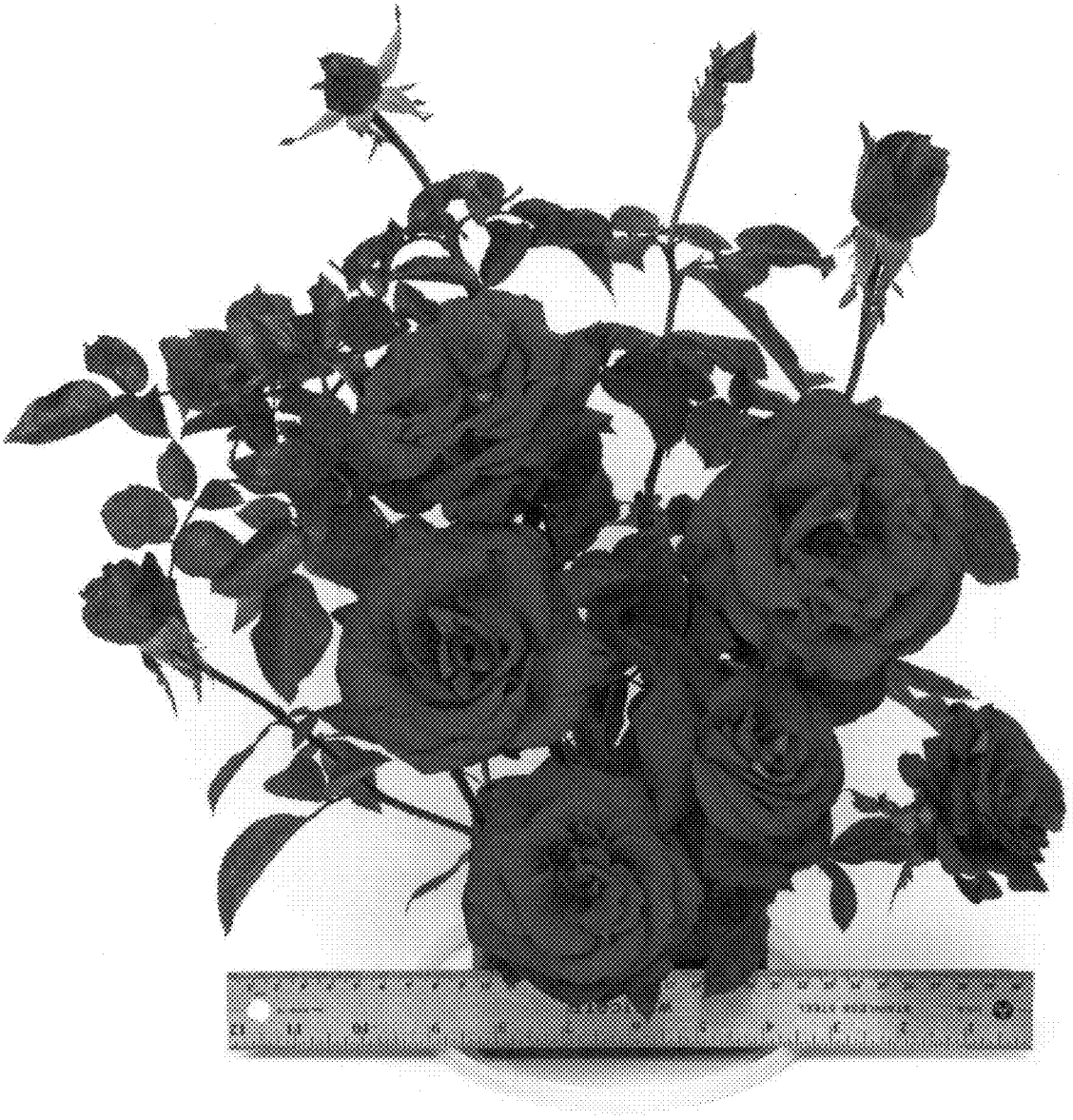

* * * * *